United States Patent [19]

Theriot

[11] Patent Number: 5,396,013
[45] Date of Patent: Mar. 7, 1995

[54] OLEFIN OLIGOMERIZATION PROCESS

[75] Inventor: Kevin J. Theriot, Baton Rouge, La.

[73] Assignee: Albemarle Corporation, Richmond, Va.

[21] Appl. No.: 90,648

[22] Filed: Jul. 12, 1993

[51] Int. Cl.6 ............................ C07C 2/04; C07C 2/02
[52] U.S. Cl. ................................... 585/510; 585/520; 585/525
[58] Field of Search ........................ 585/510, 520, 525

[56] References Cited

U.S. PATENT DOCUMENTS

| | | |
|---|---|---|
| 2,500,161 | 3/1950 | Seger et al. |
| 2,500,163 | 3/1950 | Garwood. |
| 2,766,312 | 10/1956 | Serniuk. |
| 2,806,072 | 9/1957 | Cohen et al. |
| 3,382,291 | 5/1968 | Brennan. |
| 4,172,855 | 10/1979 | Shubkin et al. ............ 585/16 |
| 5,068,487 | 11/1991 | Theriot ........................ 585/510 |
| 5,095,172 | 3/1992 | Lanier et al. ................. 585/510 |
| 5,171,918 | 12/1992 | Shubkin et al. .............. 585/510 |
| 5,191,140 | 3/1993 | Akatsu et al. ................ 585/525 |
| 5,286,823 | 2/1994 | Rath ............................ 585/510 |

*Primary Examiner*—Helen M. S. Sneed
*Assistant Examiner*—E. D. Irzinski
*Attorney, Agent, or Firm*—Richard J. Hammond

[57] ABSTRACT

A process for making an $\alpha$-olefin oligomer comprises contacting a $C_6$ to $C_{20}$ $\alpha$-olefin monomer with a catalyst which includes boron trifluoride, a protic promotor and a polyether.

10 Claims, No Drawings

OLEFIN OLIGOMERIZATION PROCESS

This invention relates generally to the preparation of alpha-olefin oligomers which are useful as synthetic lubricants and functional fluids and more particularly to a $BF_3$-promoter catalyst system which uses a polyether modifier to control the oligomer product distribution and provide higher percentages of lower oligomers.

Alpha-olefin oligomers and their use as synthetic lubricants ("synlubes") are well-known. The oligomers are usually hydrogenated in order to improve their stability. Early reports of such synlubes are in Seger et al. U.S. Pat. No. 2,500,161 and Garwood U.S. Pat. No. 2,500,163. U.S. Pat. No. 2,766,312 describes the oligomerization of α-olefins in a Group IV metal oxide bed using a $BF_3$-protic promoter catalyst. Promoters include water, carboxylic acid, alkyl halides, alcohols and ethers. U.S. Pat. No. 2,806,072 discloses the dimerization of $C_6$–$C_{12}$ polypropylenes using a preformed $BF_3$-dialkylether catalyst. U.S. Pat. No. 3,382,291 describes the oligomerization of olefins using $BF_3$-promoter catalyst complexes which include acid anhydrides, esters, ketones and aldehydes. U.S. Pat. No. 4,172,855 describes $BF_3$-promoter catalysts for grafting a second α-olefin onto $C_6$–$C_{12}$ α-olefin dimer to form a low volatility lubricating oil. The promoters include glycol ethers such as ethylene glycol monomethyl ether, propylene glycol monoethyl ether, and di-isobutyl ether.

The particular application for which the oligomer oils are used depends upon their viscosity, with viscosities of about 2–10 cSt at 100° C. being preferred for general lubricating oil applications. These materials are mixtures of different percentages of dimer, trimer, tetramer, pentamer and higher oligomers, which oligomers are produced in different proportions in the oligomerization process. In order to increase the viscosity, processes are used which either produce more of the higher oligomers or some of the lower oligomers are removed such as by distillation. Most lower viscosity dimer products are obtained as by-products of the production of higher viscosity synthetic oils. Due to the increasing use of dimers in applications such as low temperature lubricants and drilling fluids, methods for their preferential production are of interest. It is known that higher temperatures favor dimer production, but such higher temperatures can cause corrosion of production equipment. U.S. Pat. No. 5,068,487 discloses a process for making predominantly dimers and trimers of α-olefins using an alcohol alkoxylate promoted $BF_3$ catalyst. U.S. Pat. No. 5,191,140 discloses a process for making α-olefin oligomers which uses $BF_3$ promoted by at least two of water, alcohols and anhydrides to peak the reaction at lower molecular weight product.

The discovery has now been made that polyethers will moderate $BF_3$ catalyzed oligomerizations to provide either predominantly dimer or trimer containing oligomers.

In accordance with this invention there is provided a process for making an α-olefin oligomer which comprises contacting an α-olefin monomer which contains from about 6 to 20 carbon atoms with a catalyst comprising boron trifluoride, a protic promoter and a polyether.

The olefins used in making the oligomers are predominantly (at least 50 mole percent) $C_6$ to $C_{20}$ straight chain monoolefinically unsaturated hydrocarbons in which the olefinic unsaturation occurs at the 1- or alpha-position of the straight carbon chain. Such alpha-olefins are commercially available and can be made by the thermal cracking of paraffinic hydrocarbons or by the well-known Ziegler ethylene chain growth process. Individual olefins may be used as well as mixtures of such olefins. Examples of such olefins are 1-hexene, 1-heptene, 1-octene, 1-nonene, 1-decene, 1-dodecene, 1-hexadecene and 1-tetradecene. The more preferred normal-alpha-olefin monomers are those containing about 8–14 carbon atoms. The most preferred olefin monomer is 1-decene.

The olefin monomers can also contain minor amounts of up to about 50, and usually less than 25 mole percent, of internal olefins and vinylidene olefins.

The olefin is contacted as known in the art with a catalytic amount of boron trifluoride which should be at least about 0.002 moles per mole of olefin. Preferably, the reaction mixture is saturated with $BF_3$. To be effective, the boron trifluoride is used in combination with a protic promoter such as water, carboxylic acids, mineral acids, alcohols, phenols, carboxylic acid esters and anhydrides, ketones and aldehydes. Preferred are water and $C_1$ to $C_{24}$ alcohols and, more preferably, $C_1$ to $C_{12}$ alcohols (e.g. methanol, ethanol, n-propanol, isopropanol, n-butanol, isobutanol, n-hexanol, 2-ethylhexanol, n-decanol, n-dodecanol, and the like). The amount of promoter should be an amount which is effective to cause the $BF_3$ to act as an oligomerization catalyst, for example, from about 0.001 to 0.040 moles per mole of α-olefin monomers. In general, the $BF_3$ is used in molar excess to the amount of promoter. This can be accomplished by using a closed reactor and a small $BF_3$ pressure over the reaction mixture. The promoter can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution with temperatures of about 45° C. and above favoring the production of lower oligomers, namely dimer. Preferred reaction temperatures and pressures are about 20° to 65° C. and 5 to 100 psig.

Preferred polyether modifiers can be defined by the formula:

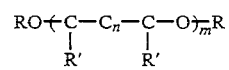

where each R is individually a hydrocarbyl group and, preferably, a $C_1$ to $C_{30}$ alkyl or cycloalkyl group or a $C_6$ to $C_{30}$ aryl group; each R′ is individually hydrogen or a hydrocarbyl group or, taken together, form a hydrocarbyl ring; also, R and R′ taken together can form a cyclic ether, when R′ is a hydrocarbyl group, it is preferably a $C_1$ to $C_{30}$ alkyl or cycloalkyl group or a $C_6$ to $C_{30}$ aryl group; n=0, 1, 2, or 3 and m=1 to 8. Non-limiting examples of such polyethers include 1,2-dimethoxyethane, diethylene glycol diethyl ether, 1,2-diethoxyethane, triethylene glycol diethyl ether, 1,2-dimethoxypropane, 1,2-dimethoxybenzene, 1,3-dimethoxycyclohexane, methyl tetrahydrofuryl ether, 1,3-dimethoxybutane, 2,3-dimethoxybutane, and the like.

The polyether modifiers are used in mole ratios of promoter to modifier which are selected to peak the oligomers at either dimer or trimer. The ratios will vary somewhat depending upon the particular combination of promoter and polyether which are used. In general, there is a range of ratios of promoter to polyether which will peak dimer. Above and below such ratios, the product will peak at trimer. For example, when using a combination of n-butanol and 1,2-dimethoxyethane, mole ratios of alcohol to polyether of up to about 1 peaked trimer whereas ratios of about 1.3 to 6.5 peaked dimer. At ratios of above 6.5, trimer again became the predominant product. When diethylene glycol diethyl ether was used, a ratio of about 1 produced predominantly dimer. The ratio which will peak the process at dimer for each catalyst combination can be readily determined by running a few oligomerizations according to the procedures described in the following examples which are intended to illustrate, but not limit, the process of the invention.

EXAMPLES 1 TO 10

1-Decene, 1-butanol (1.0 mol % based on decene), and the appropriate amount of polyether (see Table I), were charged into the reactor which was then assembled and purged with $N_2$. The reactor contents were brought up to the appropriate reaction temperature by a heating coil circulating system. The stirred reactor was then pressurized with $BF_3$ (10 psig) via a sparge tube located below the surface of the liquid. The reaction was stopped after 2 hours by venting the $BF_3$ through a caustic scrubber and quenching the reactor contents with 5% aqueous NaOH. The oligomer content of the final product was then determined by GC.

Comparative examples were run with no ether modifier at temperatures of 45° and 25° C. (Comparisons 1 and 2). A comparative example was run using a monoether (Comparison 3). Without an ether modifier, the dimer content was only 17% even at a reaction temperature of 45° C. Using a mono-ether (dibutyl ether) had little effect on the reaction. This illustrates the importance of using a polyether as the moderator.

and a polyether in a mole ratio of promoter to polyether of from about 0.5 to 10, so as to form said oligomer product.

2. The process of claim 1 wherein the mole ratio of protic promoter to polyether is selected such that the oligomer is predominantly dimer.

3. The process of claim 2 wherein the polyether is 1,2-dimethoxyethane and the mole ratio of protic promoter to polyether is from greater than about 1 to about 6.5.

4. The process of claim 3 wherein the mole ratio of protic promoter to 1,2-dimethoxyethane is from about 1.3 to 4.0.

5. The process of claim 2 wherein the polyether is diethylene glycol diethyl ether and the mole ratio of protic promoter to diethylene glycol diethyl ether is from about 0.5 to 4.0.

6. The process of claim 1 wherein the mole ratio of protic promoter to polyether is selected such that the oligomer is predominantly trimer.

7. The process of claim 1 wherein the α-olefin is 1-decene.

8. The process of claim 1 wherein the polyether has the formula:

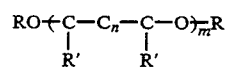

where each R is individually a $C_1$ to $C_{30}$ alkyl or cycloalkyl group or a $C_6$ to $C_{30}$ aryl group or taken with an R' forms a cyclic ether; each R' is individually hydrogen or a $C_1$ to $C_{30}$ alkyl or cycloalkyl group or a $C_6$ to $C_{30}$ aryl group or, taken together, form a hydrocarbyl ring; $n=0, 1, 2,$ or $3$ and $m=1$ to $8$.

9. The process of claim 1 wherein the reaction temperature is from about 0° to 200° C. and the pressure is

TABLE I

| | | | Temp. | G.C. Area % | | | | ROH/PE |
|---|---|---|---|---|---|---|---|---|
| Example | ROH[1] | PE[6] | °C. | Dimer | Trimer | Tetramer-plus | Conversion | mole ratio |
| 1 | BuOH[2] | DME[3] | 45 | 30 | 44 | 12 | 86 | 0.67 |
| 2 | BuOH | DME | 45 | 32 | 47 | 10 | 89 | 1.0 |
| 3 | BuOH | DME | 45 | 41 | 33 | 9 | 84 | 1.33 |
| 4 | BuOH | DME | 45 | 53 | 29 | 7 | 91 | 2.0 |
| 5 | BuOH | DME | 45 | 46 | 36 | 10 | 93 | 4.0 |
| 6 | BuOH | DME | 45 | 34 | 46 | 14 | 95 | 10.0 |
| 7 | BuOH | DME | 25 | 9 | 51 | 36 | 96 | 1.0 |
| 8 | BuOH | DME | 35 | 17 | 55 | 23 | 95 | 1.0 |
| 9 | BuOH | EEE[4] | 45 | 64 | 21 | 2 | 89 | 1.0 |
| 10 | BuOH | EEE | 45 | 51 | 34 | 8 | 95 | 2.0 |
| Comparison 1 | BuOH | — | 45 | 17 | 58 | 23 | 98 | — |
| Comparison 2 | BuOH | — | 25 | 3 | 46 | 51 | 99 | — |
| Comparison 3 | BuOH | DBE[5] | 45 | 22 | 55 | 19 | 96 | 1.0 |

[1]The total ROH concentration in all reactions is 1.0 mol % based on 1-decene.
[2]1-Butanol
[3]1,2-Dimethoxyethane
[4]2-Ethoxyethyl ether (diethylene glycol diethyl ether)
[5]Dibutyl ether
[6]PE = polyether

What is claimed is:

1. A process for making an α-olefin oligomer comprising reacting an α-olefin monomer containing from about 6 to 20 carbon atoms in the presence of a catalyst comprising, at least about 0.002 moles of boron trifluoride per mole of said monomer, from about 0.001 to 0.04 moles of a protic promoter per mole of said monomer, from atmospheric to 1,000 psig.

10. The process of claim 1 wherein the reaction temperature is from about 20° to 65° C., the pressure is from about 5 to 100 psig; and the reaction mixture is saturated with $BF_3$.

* * * * *